(12) United States Patent
Choi et al.

(10) Patent No.: US 12,385,030 B2
(45) Date of Patent: Aug. 12, 2025

(54) PROMOTER VARIANT FOR CONSTITUTIVE EXPRESSION AND USES THEREOF

(71) Applicant: DAESANG CORPORATION, Seoul (KR)

(72) Inventors: Eun Seok Choi, Seoul (KR); Ji Ha Lee, Seoul (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 18/723,639

(22) PCT Filed: Apr. 7, 2023

(86) PCT No.: PCT/KR2023/004707
§ 371 (c)(1),
(2) Date: Jun. 24, 2024

(87) PCT Pub. No.: WO2024/135948
PCT Pub. Date: Jun. 27, 2024

(65) Prior Publication Data
US 2025/0109391 A1    Apr. 3, 2025

(30) Foreign Application Priority Data
Dec. 20, 2022   (KR) .................. 10-2022-0179126

(51) Int. Cl.
*C12N 9/90* (2006.01)
*C12N 15/70* (2006.01)
*C12P 19/02* (2006.01)
*C12P 19/24* (2006.01)

(52) U.S. Cl.
CPC ............ *C12N 9/90* (2013.01); *C12N 15/70* (2013.01); *C12P 19/02* (2013.01); *C12P 19/24* (2013.01)

(58) Field of Classification Search
CPC .... C12N 9/90; C12N 15/70; C12N 2830/001; C12P 19/02; C12P 19/24; C12Y 501/03
See application file for complete search history.

(56) References Cited

U.S. PATENT DOCUMENTS

| 6,787,643 | B2 | 9/2004 | Dillon et al. |
| 8,236,940 | B2 | 8/2012 | Sung et al. |
| 2010/0196956 | A1 | 8/2010 | Sung et al. |
| 2022/0307062 | A1 | 9/2022 | Youn et al. |

FOREIGN PATENT DOCUMENTS

| KR | 10-0972843 B1 | 7/2010 |
| KR | 10-2018-0117190 A | 10/2018 |
| KR | 10-2021-0050476 A | 5/2021 |
| KR | 10-2254411 B1 | 5/2021 |
| KR | 10-2021-0132405 A | 11/2021 |
| WO | 2009/021977 A1 | 2/2009 |

OTHER PUBLICATIONS

Notice of Allowance for KR 10-2022-0179126 dated Jul. 16, 2024.
International Search Report for PCT/KR2023/004707 dated Sep. 8, 2023.

*Primary Examiner* — Iqbal H Chowdhury
(74) *Attorney, Agent, or Firm* — Sughrue Mion, PLLC

(57) ABSTRACT

The present disclosure provides a novel promoter variant in which some nucleotides are inserted, deleted, or substituted in a twin arginine translocase A (tatA) gene promoter of *Escherichia coli*. According to the present disclosure, the novel promoter variant can constitutively high-express a target protein, particularly an enzyme, in *Escherichia coli*. Therefore, by using a recombinant strain transformed with an expression vector including the novel promoter variant according to the present disclosure, it is possible to economically mass-produce a target protein, particularly an enzyme. For example, by using a recombinant strain transformed with an expression vector including the novel promoter variant according to the present disclosure, it is possible to economically mass-produce allulose epimerase or economically mass-produce allulose from fructose.

9 Claims, 4 Drawing Sheets
Specification includes a Sequence Listing.

[Figure 1]
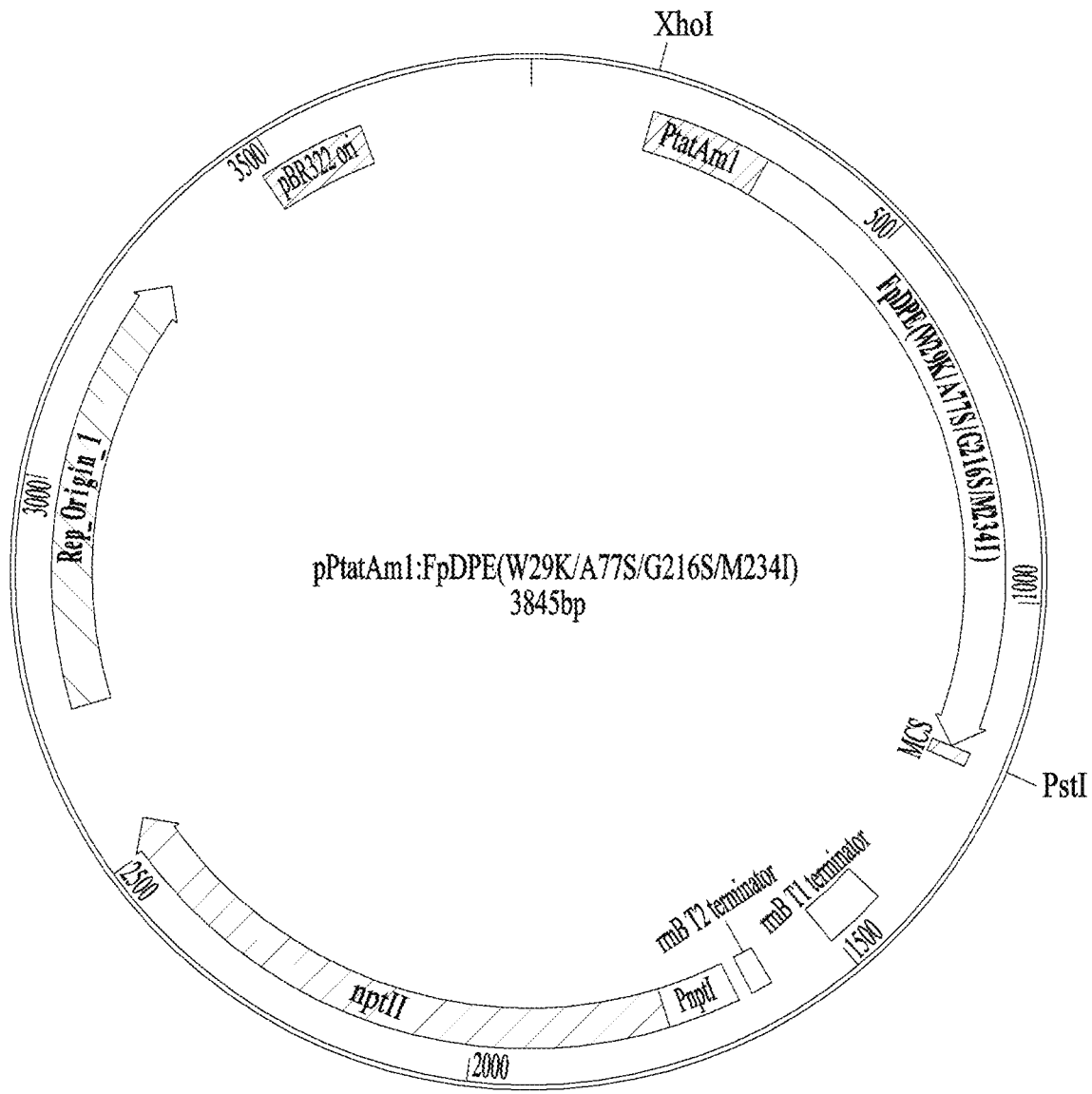

[Figure 2]
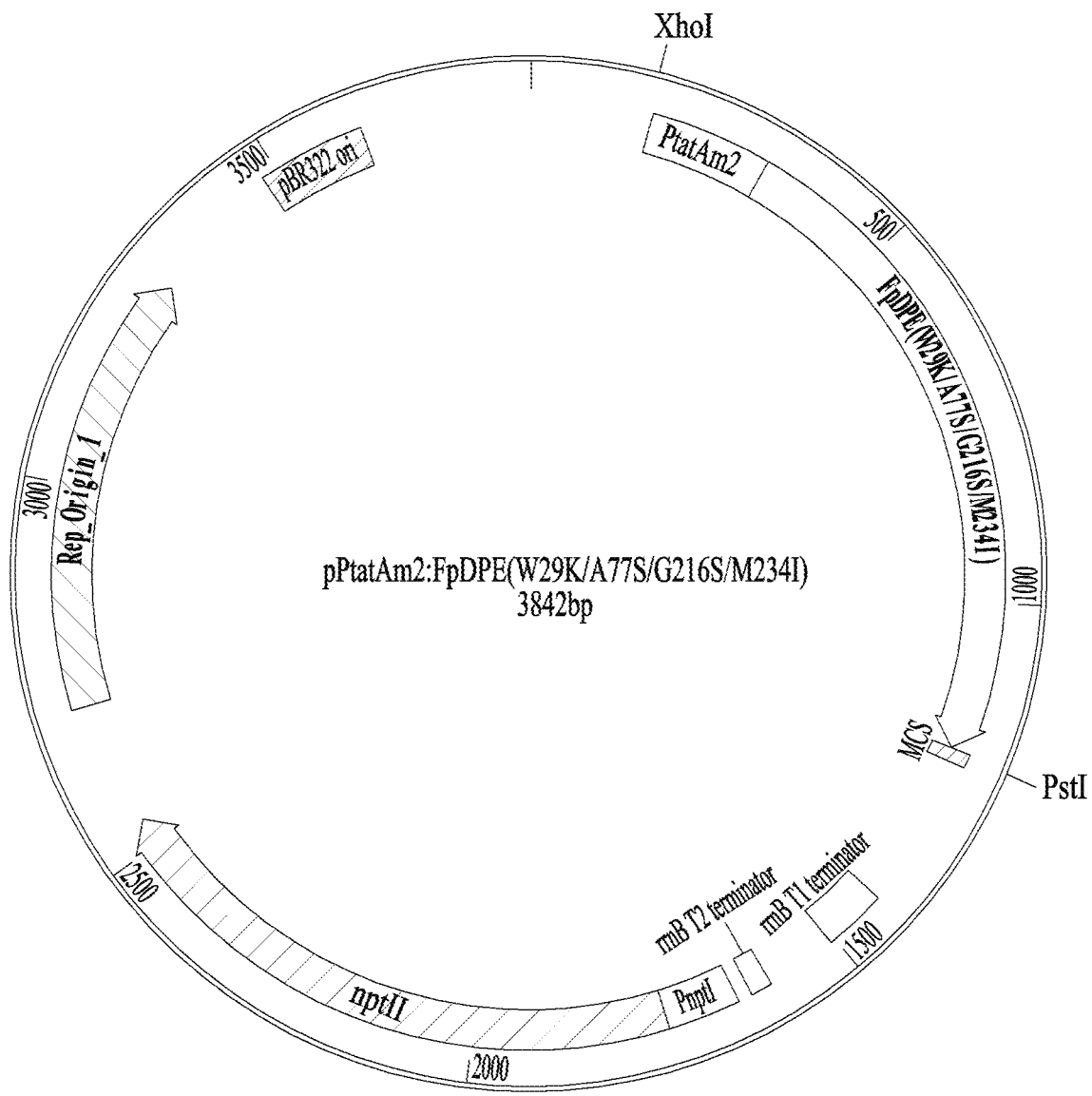

[Figure 3]
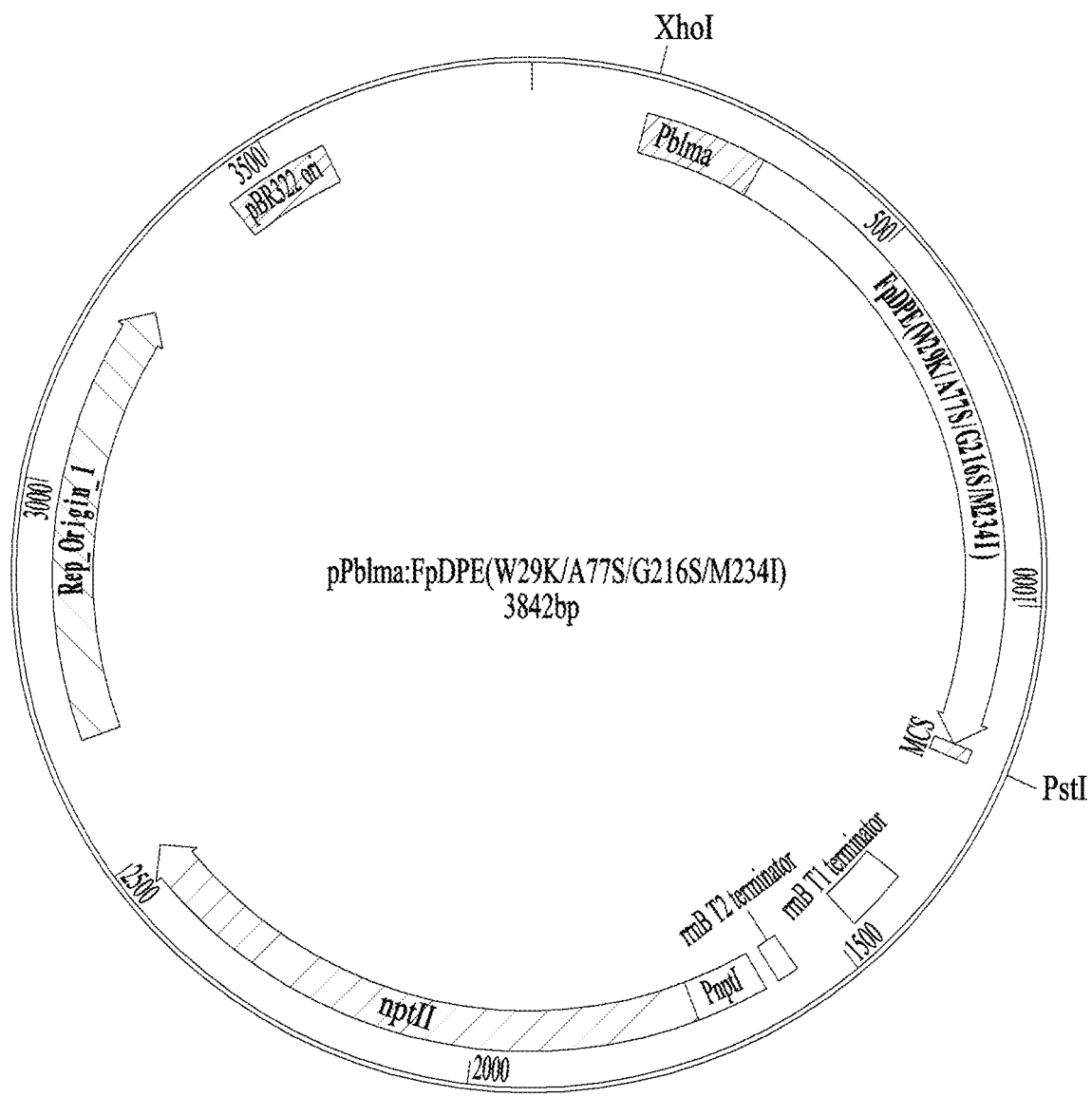

[Figure 4]
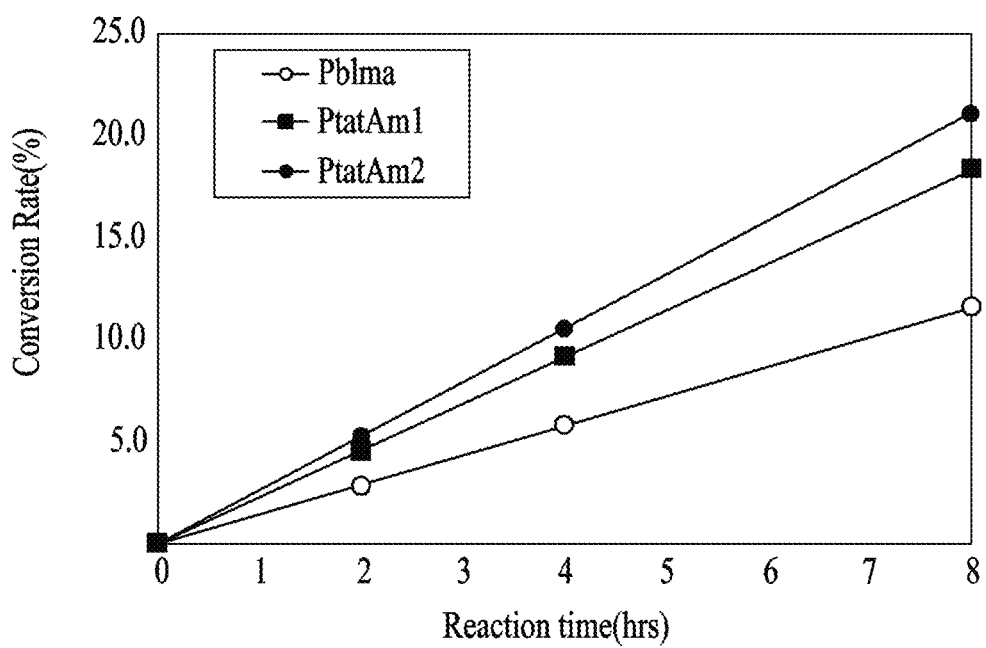

SEQUENCE LISTING

```
Sequence total quantity: 26
SEQ ID NO: 1            moltype = DNA  length = 160
FEATURE                 Location/Qualifiers
source                  1..160
                        mol_type = genomic DNA
                        organism = Escherichia coli
SEQUENCE: 1
acctgaatgg gggttgatgc ccggctggtt aatggcaggt ggtctgatcg cctggtttgt   60
cggttggcgc aaaacacgct gatttttca tcgctcaagg cgggccgtgt aacgtataat  120
gcggctttgt ttaatcatca tctaccacag aggaacatgt                        160

SEQ ID NO: 2            moltype = DNA  length = 115
FEATURE                 Location/Qualifiers
source                  1..115
                        mol_type = genomic DNA
                        organism = Bacillus licheniformis
SEQUENCE: 2
ggtgtctcat tctgttaccg ttaacagctg aaaatgattg ttcctgttac cgccgtcatg   60
```

```
ataatttcag aataaaagcc ggtttatcac agccggacaa ccaaaagggg gaaac        115

SEQ ID NO: 3             moltype = AA  length = 294
FEATURE                  Location/Qualifiers
source                   1..294
                         mol_type = protein
                         organism = Flavonifractor plautii
SEQUENCE: 3
MNPIGMHYGF WSHNWDEIAY IPLMEKLAWL GFDICEVASA EWGYYDDARL RELKACADHN    60
GLGITYSIGL EAKYDLASDD PAVRENGIRH VTRILESMPK VGAAILNGVS YAGWQALPDH   120
GITLDEKRRK EELALESMSR LMKVAEDCGV LYCCEVVNRF EQYLLNTAKE GVEFVKRLGS   180
PNARVLLDTF HMNIEEDSMV DAILEAGPWL GHFHVGENNR RPAGSTNRLP WKDMAAALKQ   240
VNYQGAIVME PFVLMGGTIP YDIKVWRDLS GGAGEAGLDE MAGRACRFLK ELTA         294

SEQ ID NO: 4             moltype = DNA  length = 885
FEATURE                  Location/Qualifiers
source                   1..885
                         mol_type = genomic DNA
                         organism = Flavonifractor plautii
SEQUENCE: 4
atgaacccga ttggaatgca ctacggcttc tggagccaca actgggacga gattgcatac    60
ataccctga tggagaagct ggcctggctg gctttgaca tctgcgaggt ggcctccgcc    120
gagtgggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtggggcgg ccatcctcaa cggcgtgtcc tacgccgggt ggcaggccct gcccgaccac    360
ggaatcaccc tggacgagaa cgccgcaag gaggagcttg ccctgagtc catgtcccgg    420
ctcatgaagg tggcggagga ctgcggcgtg ctctactgct gcgaggtggt caaccgcttc    480
gagcagtacc tgctcaacac cgccaaagag ggcgtggagt ttgtcaagcg cctgggcagt    540
cccaacgcc gggtgctgct ggataccttc cacatgaaca tcgaggagga cagcatggtg    600
gacgccattc tggaggcggg cccctggctg gggcatttcc acgtggggga gaacaaccgc    660
cgccccgccg gctccaccaa ccgcctgccc tggaaggaca tggccgccgc cctcaagcag    720
gtgaactacc aggggggccat tgtgatggag cccttcgtgc tcatggggggg taccattccc    780
tatgatatca aggtctggcg ggatctcagc ggcggggccg ggaggccgg ctggacgag    840
atggcgggcc gggcctgccg gttcctcaag gagctgaccg cgtaa                 885

SEQ ID NO: 5             moltype = AA  length = 294
FEATURE                  Location/Qualifiers
source                   1..294
                         mol_type = protein
                         organism = synthetic construct
SEQUENCE: 5
MNPIGMHYGF WSHNWDEIAY IPLMEKLAKL GFDICEVASA EWGYYDDARL RELKACADHN    60
GLGITYSIGL EAKYDLASDD PAVRENGIRH VTRILESMPK VGAAILNGVS YAGWQALPDH   120
GITLDEKRRK EELALESMSR LMKVAEDCGV LYCCEVVNRF EQYLLNTAKE GVEFVKRLGS   180
PNARVLLDTF HMNIEEDSMV DAILEAGPWL GHFHVSENNR RPAGSTNRLP WKDIAAALKQ   240
VNYQGAIVME PFVLMGGTIP YDIKVWRDLS GGAGEAGLDE MAGRACRFLK ELTA         294

SEQ ID NO: 6             moltype = DNA  length = 885
FEATURE                  Location/Qualifiers
source                   1..885
                         mol_type = other DNA
                         organism = synthetic construct
SEQUENCE: 6
atgaacccga ttggaatgca ctacggcttc tggagccaca actgggacga gattgcatac    60
ataccctga tggagaagct ggccaaactg ggctttgaca tctgcgaggt ggcctccgcc    120
gagtgggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtggggcgg ccatcctcaa cggcgtgtcc tacgccgggt ggcaggccct gcccgaccac    360
ggaatcaccc tggacgagaa cgccgcaag gaggagcttg ccctgagtc catgtcccgg    420
ctcatgaagg tggcggagga ctgcggcgtg ctctactgct gcgaggtggt caaccgcttc    480
gagcagtacc tgctcaacac cgccaaagag ggcgtggagt ttgtcaagcg cctgggcagt    540
cccaacgcc gggtgctgct ggataccttc cacatgaaca tcgaggagga cagcatggtg    600
gacgccattc tggaggcggg cccctggctg gggcatttcc acgtgagcga gaacaaccgc    660
cgccccgccg gctccaccaa ccgcctgccc tggaaggaca ttgccgccgc cctcaagcag    720
gtgaactacc aggggggccat tgtgatggag cccttcgtgc tcatggggggg taccattccc    780
tatgatatca aggtctggcg ggatctcagc ggcggggccg ggaggccgg ctggacgag    840
atggcgggcc gggcctgccg gttcctcaag gagctgaccg cgtaa                 885

SEQ ID NO: 7             moltype = AA  length = 294
FEATURE                  Location/Qualifiers
source                   1..294
                         mol_type = protein
                         organism = synthetic construct
SEQUENCE: 7
MNPIGMHYGF WSHNWDEIAY IPLMEKLAKL GFDICEVASA EWGYYDDARL RELKACADHN    60
GLGITYSIGL EAKYDLSSDD PAVRENGIRH VTRILESMPK VGAAILNGVS YAGWQALPDH   120
GITLDEKRRK EELALESMSR LMKVAEDCGV LYCCEVVNRF EQYLLNTAKE GVEFVKRLGS   180
```

```
PNARVLLDTF HMNIEEDSMV DAILEAGPWL GHFHVSENNR RPAGSTNRLP WKDIAAALKQ    240
VNYQGAIVME PFVLMGGTIP YDIKVWRDLS GGAGEAGLDE MAGRACRFLK ELTA         294

SEQ ID NO: 8            moltype = DNA   length = 885
FEATURE                 Location/Qualifiers
source                  1..885
                        mol_type = other DNA
                        organism = synthetic construct
SEQUENCE: 8
atgaacccga ttggaatgca ctacggcttc tggagccaca actgggacga gattgcatac    60
ataccctga tggagaagct ggccaaactg gctttgaca tctgcgaggt ggcctccgcc    120
gagtggggct attacgacga cgccaggctg cgggagctga aggcctgcgc cgatcacaac   180
ggcctgggca tcacctattc catcggcctg gaggccaaat acgacctgag cagcgacgat   240
ccggcggtgc gggagaacgg catccgccat gtcacccgca tcctggagag catgcccagg   300
gtggggggcgg ccatcctcaa cggcgtgtcc tacgccgggt ggcaggccct gcccgaccac   360
ggaatcaccc tggacgagaa cgccgcaag gaggagcttg ccctggagtc catgtcccgg   420
ctcatgaagg tggcggagga ctgcggcgtg ctctactgct gcgaggtggt caaccgcttc   480
gagcagtacc tgctcaacac cgccaaagag ggcgtggagt ttgtcaagcg cctgggcagt   540
cccaacgccc gggtgctgct ggataccttc cacatgaaca tcgaggagga cagcatggtg   600
gacgccattc tggaggcggg ccctggctg gggcatttcc acgtgagcga gaacaaccgc   660
cgccccgccg gctccaccaa ccgcctgccc tggaaggaca ttgccgccgc cctcaagcag   720
gtgaactacc aggggccat tgtgatggag ccctttgtcc tcatgggggg taccattccc   780
tatgatatca aggtctggcg ggatctcagc ggcggggccg gggaggccgg gctggacgag   840
atggcgggcc gggcctgccg gttcctcaag gagctgaccg cgtaa                   885

SEQ ID NO: 9            moltype = DNA   length = 161
FEATURE                 Location/Qualifiers
source                  1..161
                        mol_type = other DNA
                        organism = synthetic construct
SEQUENCE: 9
acctgaatgg gggttgatgc ccggctggtt aatggcaggt ggtctgatcg cctggtttgt    60
cggttggcgc aaaacacgct gatttttca tcgctcaagg cgggccgtgt aacgtataat   120
gcggctttgt ttaatcatca tctaccacag aggaacatgt c                      161

SEQ ID NO: 10           moltype = DNA   length = 158
FEATURE                 Location/Qualifiers
source                  1..158
                        mol_type = other DNA
                        organism = synthetic construct
SEQUENCE: 10
acctgaatgg gggttgatgc ccggctggtt aatggcaggt ggtctgatcg cctggtttgt    60
cggttggcgc aaaacacgct gatttttca tcgctcaagg cgggccgtgt aacgtataat   120
gcggctttgt ttaatcatca tctacgaagg aggaacat                          158

SEQ ID NO: 11           moltype = DNA   length = 20
FEATURE                 Location/Qualifiers
source                  1..20
                        mol_type = other DNA
                        organism = synthetic construct
SEQUENCE: 11
acctgaatgg gggttgatgc                                                20

SEQ ID NO: 12           moltype = DNA   length = 19
FEATURE                 Location/Qualifiers
source                  1..19
                        mol_type = other DNA
                        organism = synthetic construct
SEQUENCE: 12
acatgttcct ctgtggtag                                                 19

SEQ ID NO: 13           moltype = DNA   length = 20
FEATURE                 Location/Qualifiers
source                  1..20
                        mol_type = other DNA
                        organism = synthetic construct
SEQUENCE: 13
ggtgtctcat tctgttaccg                                                20

SEQ ID NO: 14           moltype = DNA   length = 20
FEATURE                 Location/Qualifiers
source                  1..20
                        mol_type = other DNA
                        organism = synthetic construct
SEQUENCE: 14
gtttcccct tttggttgtc                                                 20

SEQ ID NO: 15           moltype = DNA   length = 32
FEATURE                 Location/Qualifiers
```

```
                                   -continued
source               1..32
                     mol_type = other DNA
                     organism = synthetic construct
SEQUENCE: 15
aatacgacct gagcagcgac gatccggcgg tg                              32

SEQ ID NO: 16        moltype = DNA   length = 33
FEATURE              Location/Qualifiers
source               1..33
                     mol_type = other DNA
                     organism = synthetic construct
SEQUENCE: 16
gatcgtcgct gctcaggtcg tatttggcct cca                             33

SEQ ID NO: 17        moltype = DNA   length = 29
FEATURE              Location/Qualifiers
source               1..29
                     mol_type = other DNA
                     organism = synthetic construct
SEQUENCE: 17
gcatgccata tgaacccgat tggaatgca                                  29

SEQ ID NO: 18        moltype = DNA   length = 32
FEATURE              Location/Qualifiers
source               1..32
                     mol_type = other DNA
                     organism = synthetic construct
SEQUENCE: 18
gcatgcctcg agcgcggtca gctccttgag ga                              32

SEQ ID NO: 19        moltype = DNA   length = 32
FEATURE              Location/Qualifiers
source               1..32
                     mol_type = other DNA
                     organism = synthetic construct
SEQUENCE: 19
tttgcgctcg agacctgaat ggggttgat gc                               32

SEQ ID NO: 20        moltype = DNA   length = 39
FEATURE              Location/Qualifiers
source               1..39
                     mol_type = other DNA
                     organism = synthetic construct
SEQUENCE: 20
tgcattccaa tcgggttcat acatgttcct ctgtggtag                       39

SEQ ID NO: 21        moltype = DNA   length = 39
FEATURE              Location/Qualifiers
source               1..39
                     mol_type = other DNA
                     organism = synthetic construct
SEQUENCE: 21
ctaccacaga ggaacatgta tgaacccgat tggaatgca                       39

SEQ ID NO: 22        moltype = DNA   length = 31
FEATURE              Location/Qualifiers
source               1..31
                     mol_type = other DNA
                     organism = synthetic construct
SEQUENCE: 22
gcatgctgca gttacgcggt cagctccttg a                               31

SEQ ID NO: 23        moltype = DNA   length = 32
FEATURE              Location/Qualifiers
source               1..32
                     mol_type = other DNA
                     organism = synthetic construct
SEQUENCE: 23
tttgcgctcg agggtgtctc attctgttac cg                              32

SEQ ID NO: 24        moltype = DNA   length = 40
FEATURE              Location/Qualifiers
source               1..40
                     mol_type = other DNA
                     organism = synthetic construct
SEQUENCE: 24
tgcattccaa tcgggttcat gtttccccct tttggttgtc                      40

SEQ ID NO: 25        moltype = DNA   length = 40
```

```
FEATURE             Location/Qualifiers
source              1..40
                    mol_type = other DNA
                    organism = synthetic construct
SEQUENCE: 25
gacaaccaaa aggggggaaac atgaacccga ttggaatgca                              40

SEQ ID NO: 26       moltype = DNA   length = 31
FEATURE             Location/Qualifiers
source              1..31
                    mol_type = other DNA
                    organism = synthetic construct
SEQUENCE: 26
gcatgctgca gttacgcggt cagctccttg a                                        31
```

PROMOTER VARIANT FOR CONSTITUTIVE EXPRESSION AND USES THEREOF

CROSS REFERENCE TO RELATED APPLICATIONS

This application is a National Stage of International Application No. PCT/KR2023/004707 filed Apr. 7, 2023, claiming priority based on Korean Patent Application No. 10-2022-0179126 filed Dec. 20, 2022.

INCORPORATION BY REFERENCE OF SEQUENCE LISTING

The instant application contains a Sequence Listing which has been filed electronically in xml format and is hereby incorporated by reference in its entirety. Said xml copy, created on Jun. 24, 2024, is named Q299941 sequence listing as filed.xml and is 28,026 bytes in size.

TECHNICAL FIELD

The present disclosure relates to a novel promoter variant and the like, and more particularly, to a novel promoter variant capable of constitutively high-expressing a target protein and various uses thereof.

BACKGROUND ART

With the development of molecular biology, various mechanisms that regulate gene expression have been found. The gene expression refers to a series of processes of synthesizing proteins according to a code input into the gene through transcription and translation that occur within a cell. In particular, the transcription process is an initial step of gene expression, and is initiated when RNA polymerase binds to a promoter sequence located upstream of the gene with the aid of several auxiliary factors, and a transcription factor (TF) is known to bind directly to the promoter sequence as one of these auxiliary factors. In particular, since regulation of gene expression in prokaryotes occurs primarily at the transcription stage, researchers continue to find new transcription factors and promoters.

Industrially, in order to produce foreign proteins such as enzymes, transformants produced by transforming prokaryotes such as *E. coli* with a pET-type expression vector including a foreign protein gene are used as an expression system. The prokaryotic expression system transformed with the pET-type expression vector generally has a disadvantage of requiring expensive expression inducers such as isopropyl-β-D-thiogalactopyranoside (IPTG), and requiring precise control of inducer concentration, equipment, expression induction time, etc.

Meanwhile, there has been proposed an expression system using a *Corynebacterium* strain, which is a generally recognized as safe (GRAS) strain, as a host cell to mass-produce psicose epimerase (or allulose epimerase) that has the activity of converting fructose to allulose (or psicose). Regarding a psicose epimerase (or allulose epimerase) expression system based on a *Corynebacterium* strain, in Korean Patent Registration No. 10-1656063, there is disclosed a gene expression cassette including a nucleotide sequence encoding psicose epimerase, and a regulatory sequence that is operably linked to the upstream thereof and regulates expression of the psicose epimerase in the *Corynebacterium* strain, in which the regulatory sequence consists of a transcription promoter, a first ribosome binding region (RBS) sequence, a first spacer sequence, a linker sequence, a second RBS sequence, etc. In addition, in Korean Patent Registration No. 10-1695830, there is disclosed a gene expression cassette including a nucleotide sequence encoding psicose epimerase, and a regulatory sequence that is operably linked to the upstream thereof and regulates expression of the psicose epimerase in the *Corynebacterium* strain, in which the regulatory sequence includes a transcription promoter derived from *E. coli*. However, a *Corynebacterium*-based psicose epimerase (or allulose epimerase) expression system is not suitable for an enzyme mass expression system due to a low expression level and a small range of selection of available promoters.

Therefore, for mass production of psicose epimerase (or allulose epimerase) or mass production of allulose from fructose using psicose epimerase (or allulose epimerase), there is a need for the development of a constitutive expression promoter and a constitutive expression system including the same that can stably express a foreign protein at a high level without growth inhibition under general culture conditions of an *E. coli* host cell as well as when *Corynebacterium* is used as a host cell.

DISCLOSURE

Technical Problem

The present disclosure has been derived under the technical background of the related art, and an object of the present disclosure is to provide a novel promoter variant capable of constitutively high-expressing a target protein. Another object of the present disclosure is to provide various uses of the novel promoter variant.

Technical Solution

The present inventors manufactured a recombinant expression vector by operably linking a tatA gene promoter, which was a promoter for expressing a twin arginine translocase A (tatA) gene of *Escherichia coli*, to a polynucleotide encoding allulose epimerase, and introduced the recombinant expression vector to *Escherichia coli* to be transformed. At this time, random mutations occurred in the tatA promoter or allulose epimerase gene sequence, and the present inventors obtained recombinant *Escherichia coli* transformed with various recombinant expression vectors. As a result of comparing the allulose epimerase expression activity of recombinant *Escherichia coli* transformed with a recombinant expression vector in which mutation occurred only in the tatA gene promoter and no mutation occurred in the allulose epimerase gene sequence among the recombinant expression vectors obtained through the random mutation, the present inventors confirmed that a promoter variant in which cytosine (C) was added after thymine (T), a nucleotide at position 160 in a base sequence of the tatA gene promoter, or a promoter variant in which in the base sequence of the tatA gene promoter, cytosine (C), a nucleotide at position 146 was substituted with guanine (G), cytosine (C), a nucleotide at position 148 was substituted with adenine (A), adenine (A), a nucleotide at position 149 was substituted with guanine (G), and guanine (G) and thymine (T), nucleotides at positions 159 and 160 are deleted constitutively high-expressed allulose epimerase, and then completed the present disclosure.

In order to achieve the object, one embodiment of the present disclosure provides a promoter variant consisting of a base sequence represented by SEQ ID NO: 9 or a base sequence represented by SEQ ID NO: 10. Further, one embodiment of the present disclosure provides a recombinant vector including a promoter variant consisting of a base sequence represented by SEQ ID NO: 9 or a base sequence represented by SEQ ID NO: 10. Further, one embodiment of the present disclosure provides an expression vector including a polynucleotide encoding a target protein and a promoter variant operably linked thereto and consisting of a base sequence represented by SEQ ID NO: 9 or a base sequence represented by SEQ ID NO: 10. Further, one embodiment of the present disclosure provides a recombinant strain transformed with the expression vector. Further, one embodiment of the present disclosure provides a method for producing a target protein using the recombinant strain. Further, a preferred embodiment of the present disclosure provides a method for preparing an enzymatic conversion reaction product from a substrate, including adding the recombinant strain to a substrate-containing solution and performing an enzymatic conversion reaction.

Advantageous Effects

According to the present disclosure, a novel promoter variant can constitutively high-express a target protein, particularly an enzyme, in *Escherichia coli*. Therefore, by using a recombinant strain transformed with an expression vector including a novel promoter variant according to the present disclosure, it is possible to economically mass-produce a target protein, particularly an enzyme. For example, by using a recombinant strain transformed with an expression vector including a novel promoter variant according to the present disclosure, it is possible to economically mass-produce allulose epimerase or economically mass-produce allulose from fructose.

DESCRIPTION OF DRAWINGS

FIG. 1 is a cleavage map of a recombinant expression vector pPtatAm1:FpDPE (W29K/A77S/G216S/M234I) prepared in Example of the present disclosure.

FIG. 2 is a cleavage map of a recombinant expression vector pPtatAm2:FpDPE (W29K/A77S/G216S/M234I) prepared in Example of the present disclosure.

FIG. 3 is a cleavage map of a recombinant expression vector pPblma:FpDPE (W29K/A77S/G216S/M234I) prepared in Example of the present disclosure.

FIG. 4 illustrates a conversion rate according to a reaction time when a conversion reaction of fructose to allulose is performed using recombinant *Escherichia coli* prepared in Example of the present disclosure.

MODES OF THE INVENTION

Hereinafter, the present disclosure will be described in detail.

As used herein, the term 'promoter' refers to a minimum nucleic acid sequence that is operably linked to a target nucleotide sequence that is a transcription target and regulates transcription of the target nucleotide sequence. In addition, the promoter may include promoter components sufficient to express a regulatable promoter-dependent gene induced by a cell-type specific or external signal or agent, and these components may be located at the 5' or 3' portion of the gene. The promoter includes both a conservative promoter and an inducible promoter. The promoter sequence may be derived from prokaryotes, eukaryotes or viruses. In prokaryotes, the promoter is usually defined as a binding site immediately near a transcription start site to which RNA polymerase binds.

As used herein, the term 'promoter variant' is defined as a promoter having a target protein expression activity that is different or improved from that of a basic promoter by deleting, adding, or substituting some nucleotides in a nucleic acid sequence of the basic promoter.

As used herein, the term 'homology' refers to the identity with a nucleic acid sequence of a wild type or a variant having the same activity, and the homology may be compared by calculating the homology between two or more sequences as a percentage (%) visually or by using an easily available comparison program.

As used herein, the term 'target protein' is a foreign protein and refers to a protein that cannot normally exist in a transformed strain (or host cell) expressing the protein.

As used herein, the term 'polynucleotide' refers to any non-modified or modified polyribonucleotide (RNA) or polydeoxyribonucleotide (DNA). The polynucleotide includes single- or double-stranded DNA, DNA as a mixture of single- and double-stranded regions, single- and double-stranded RNA, RNA as a mixture of single- and double-stranded regions, or hybrid molecules thereof, but is not limited thereto.

As used herein, the term 'operably linked' is defined as a state in which a promoter sequence and a nucleotide sequence encoding a target protein are functionally linked to each other so that the promoter may regulate the expression of the target protein. For example, when the promoter is capable of controlling expression of a coding sequence (i.e. when the coding sequence is under the transcriptional regulation of the promoter), the promoter is operably linked to the coding sequence, or when a ribosome binding site is located to promote translation, the ribosome binding site is operably linked to the coding sequence. The coding sequence may be operably linked to a regulatory sequence in either a sense or antisense direction.

As used herein, the term 'recombinant vector' is defined as a recombinant DNA prepared by cleaving a promoter variant or a target gene using a restriction enzyme and inserting the promoter variant or the target gene into a vector.

As used herein, the term 'cloning vector' is defined as a material capable of transporting DNA fragments into a host cell and reproducing the DNA fragments. The cloning vector may further include a polyadenylation signal, a transcription termination sequence, and a multiple cloning site. The multiple cloning site includes at least one endonuclease restriction site. In addition, the cloning vector may further include a promoter. In addition, the polynucleotide encoding the target protein within the cloning vector may be located upstream of a polyadenylation signal and a transcription termination sequence.

As used herein, the term 'expression vector' is defined as a DNA sequence necessary for transcription and translation of cloned DNA in a suitable host, and specifically, refers to a genetic construct including essential regulatory elements operably linked to an insert such that the insert is expressed when present within a cell of a subject. The expression vector may be prepared and purified using a standard recombinant DNA technique. The type of expression vector is not particularly limited as long as the expression vector has the function of expressing a desired gene and producing a desired protein in various host cells of prokaryotic and eukaryotic cells. The expression vector includes at least a promoter, a start codon, a gene encoding a desired protein, and a stop codon terminator. In addition, the expression vector may also appropriately include DNA encoding a signal peptide, an additional expression regulatory sequence, untranslated regions on the 5' and 3' sides of a desired gene, a selection marker region, a replicable unit, or the like. The selection marker region may be a selection marker gene of an antibiotic for selecting a desired vector.

As used herein, the term 'recombinant strain' refers to a cell transformed by introducing a polynucleotide encoding at least one target protein or an expression vector having the polynucleotide into a host cell. Methods for preparing a transformant by introducing the expression vector into the host cell include transient transfection, microinjection, transduction, cell fusion, calcium phosphate precipitation, liposome mediated transfection, DEAE dextran-mediated transfection, polybrene-mediated transfection, electroporation, electroinjection, chemical treatment methods such as PEG, methods using gene guns, etc., heat shock, and the like, but are not limited thereto.

As used herein, the term 'substrate' refers to any material or compound that is converted or is to be converted into another compound by the action of an enzyme. The term encompasses not only single compounds, but also combinations of compounds such as solvents, mixtures and other materials including at least one substrate, and derivatives thereof.

One aspect of the present disclosure relates to a novel promoter variant capable of constitutively high-expressing a target protein. The novel promoter variant according to one embodiment of the present disclosure consists of a base sequence represented by SEQ ID NO: 9 or SEQ ID NO: 10. The present inventors named a promoter variant consisting of the base sequence represented by SEQ ID NO: 9 as 'tatAm1,' and named a promoter variant consisting of a base sequence represented by SEQ ID NO: 10 as 'tatAm2'. In the novel promoter variant tatAm1 according to one embodiment of the present disclosure, twin arginine translocase A (tatA) gene promoter derived from *Escherichia coli* consisting of a base sequence represented by SEQ ID NO: 1 is mutated, and specifically, cytosine (C) is added after thymine (T), which is a nucleotide at position 160 in the base sequence represented by SEQ ID NO: 1. In addition, in the novel promoter variant tatAm2 according to one embodiment of the present disclosure, cytosine (C), which is a nucleotide at position 146 in the base sequence represented by SEQ ID NO: 1 is substituted with guanine (G), cytosine (C), which is a nucleotide at position 148 is substituted with adenine (A), adenine (A), which is a nucleotide at position 149 is substituted with guanine (G), and guanine (G) and thymine (T), which are nucleotides at positions 159 and 160 are deleted. The promoter variant consisting of the base sequence represented by SEQ ID NO: 9 is caused by a mutation in a ribosome-binding site (RBS) spacer, and the promoter variant consisting of the base sequence represented by SEQ ID NO: 10 is caused by a mutation in the sequence surrounding the ribosome-binding site (RBS). An expression system including the novel promoter variant according to one embodiment of the present disclosure may constitutively high-express a target protein in *Escherichia coli*. Accordingly, the novel promoter variant according to one embodiment of the present disclosure may be used as a constitutive expression promoter. The novel promoter variant according to one embodiment of the present disclosure consists of the base sequence represented by SEQ ID NO: 9 or the base sequence represented by SEQ ID NO: 10, but an equivalent range of the novel promoter variant according to one embodiment of the present disclosure is not necessarily limited thereto. For example, the equivalent range of the novel promoter variant according to one embodiment of the present disclosure includes a promoter in which some nucleotides in the base sequence represented by SEQ ID NO: 9 are substituted, inserted and/or deleted within a range in which the function of constitutively high-expressing the target protein is maintained. In addition, the equivalent range of the novel promoter variant according to one embodiment of the present disclosure includes a sequence having substantial identity to the base sequence represented by SEQ ID NO: 9. The substantial identity means that any other sequence has a sequence homology of 70% or more, 90% or more, or 98% or more with the base sequence represented by SEQ ID NO: 9 or the base sequence represented by SEQ ID NO: 10 by aligning other sequence to maximally correspond to the base sequence represented by SEQ ID NO: 9 or the base sequence represented by SEQ ID NO: 10 and analyzing the sequence thereof. It will be easily appreciated that those skilled in the art may prepare a polynucleotide having the same or similar activity within the range having the substantial homology by substituting, adding or deleting one or more bases in the base sequence of the novel promoter variant using a genetic recombination technique and the like known in the art. Comparison of such a homology may be performed by calculating a homology between two or more sequences as a percentage (%) using a commercially available computer program. Accordingly, the equivalent range of the novel promoter variant according to one embodiment of the present disclosure may include a base sequence having a homology of 70% or more, 80% or more, 90% or more, 95% or more, or 99% or more with the base sequence represented by SEQ ID NO: 9 or the base sequence represented by SEQ ID NO: 10, within a range in which the function of constitutively high-expressing the target protein is maintained.

Another aspect of the present disclosure relates to various uses of the novel promoter variants according to one embodiment of the present disclosure. The uses of the novel promoter variant according to one embodiment of the present disclosure include a recombinant vector, an expression vector, a recombinant strain, a method for producing a target protein, a method for exhibiting the function of a target protein using a recombinant strain, and the like, but are not necessarily limited thereto.

The recombinant vector according to one embodiment of the present disclosure includes a promoter variant consisting of the base sequence represented by SEQ ID NO: 9 or the base sequence represented by SEQ ID NO: 10.

The recombinant vector may be a cloning vector. The cloning vector may include a replication origin, a multi cloning site (MCS) for cloning a target protein gene, a transcription termination sequence, and a selection marker. The selective marker is used to select cells transformed with a vector, and may be used with markers that impart selectable phenotypes such as drug resistance, auxotrophy, resistance to cytotoxic agents, or expression of surface proteins. In an environment treated with a selective agent, only cells expressing the selection marker survive, so that transformed cells can be selected. For example, the selection marker may be a drug resistance gene, such as a Kanamycin antibiotic resistance gene or an Ampicillin antibiotic resistance gene.

In addition, the recombinant vector may be an expression vector. The expression vector includes a polynucleotide encoding a target protein and a promoter variant operably linked thereto and consisting of the base sequence represented by SEQ ID NO: 9. The promoter variant is preferably located upstream of the polynucleotide encoding the target protein. The target protein expressed through the expression vector according to one embodiment of the present disclosure is not greatly limited to the type thereof, and may be selected from the group consisting of, for example, proteins involved in biosynthesis or metabolism of carbohydrates, proteins involved in biosynthesis or metabolism of lipids and fatty acids, proteins involved in biosynthesis or metabolism of proteins and peptides, etc. In addition, the target protein is preferably an enzyme, considering the expression regulatory activity of the promoter variant. The type of the enzyme is not greatly limited, and may be selected from the group consisting of D-allulose 3-epimerase, D-tagatose 3-epimerase, (1→4)-alpha-D-glucan 1-alpha-D-glucosylmutase, 4-alpha-D-{(1→4)-alpha-D-glucano}trehalose trehalohydrolase, L-rhamnose isomerase, fructose-6-phosphate-3-epimerase, etc., and preferably selected from the group consisting of D-allulose 3-epimerase, (1→4)-alpha-D-glucan 1-alpha-D-glucosylmutase, and 4-alpha-D-{(1→4)-alpha-D-glucano}trehalose trehalohydrolase. Although not specifically described in the embodiment of the present disclosure, the novel promoter variant of the present disclosure expressed (1→4)-alpha-D-glucan 1-alpha-D-glucosylmutase, 4-alpha-D-{(1→4)-alpha-D-glucano}trehalose trehalohydrolase, and the like at a higher level compared to a twin arginine translocase A (tatA) gene promoter derived from *Escherichia coli* consisting of the base sequence represented by SEQ ID NO: 1. The allulose epimerase is not particularly limited to the type thereof as long as it is an enzyme having the activity of converting fructose into allulose, and may consist of, for example, an amino acid sequence represented by SEQ ID NO: 3, an amino acid sequence represented by SEQ ID NO: 5, or an amino acid sequence represented by SEQ ID NO: 7. In addition, the polynucleotide encoding the allulose epimerase may consist of a base sequence represented by SEQ ID NO: 4, a base sequence represented by SEQ ID NO: 6, or a base sequence represented by SEQ ID NO: 8. In addition, the present disclosure includes the contents disclosed in Korean Patent Registration Nos. 10-1919713, 10-2187354, 10-1656063, 10-1695830, 10-2189458, 10-1539097, 10-1539096, 10-1455759, 10-1318422, etc., with respect to the allulose epimerase and the polynucleotides encoding the same. An expression vector according to a preferred embodiment of the present disclosure has a cleavage map of FIG. 1 or a cleavage map of FIG. 2. An expression vector having the cleavage map of FIG. 1 has a structure in which a pUC-derived replication origin (ori), a promoter variant (PtatAm1) consisting of a base sequence represented by SEQ ID NO: 9, a polynucleotide [FpDPE (W29K/A77S/G216S/M234I)] encoding allulose epimerase consisting of a base sequence represented by SEQ ID NO: 8, a Kanamycin resistance gene marker (KanR), etc. are sequentially linked to each other. In addition, an expression vector having the cleavage map of FIG. 2 has a structure in which a pUC-derived replication origin (ori), a promoter variant (PtatAm2) consisting of a base sequence represented by SEQ ID NO: 10, a polynucleotide [FpDPE(W29K/A77S/G216S/M234I)] encoding allulose epimerase consisting of a base sequence represented by SEQ ID NO: 8, a Kanamycin resistance gene marker (KanR), etc. are sequentially linked to each other.

In the recombinant strain according to one embodiment of the present disclosure, a host cell is transformed by introducing an expression cassette including a polynucleotide encoding a target protein and a promoter variant operably linked thereto and consisting of a base sequence represented by SEQ ID NO: 9 or a base sequence represented by SEQ ID NO: 10, or an expression vector including the expression cassette. In the present disclosure, the host cell that may be transformed with the expression vector is not particularly limited to the type as long as the novel promoter variant according to one embodiment of the present disclosure may operate smoothly, and preferably a prokaryotic organism, and more preferably *Escherichia coli* when considering the expression regulation activity of the novel promoter variant, the introduction efficiency of DNA, the expression efficiency of the introduced DNA, etc. The *Escherichia coli* includes BL21, JM109, K-12, LE392, RR1, DH55α, W3110, or the like, but is not limited thereto.

A method for preparing a target protein according to one embodiment of the present disclosure includes culturing the above-described recombinant strain to express a target protein; and isolating the target protein from a culture medium of the recombinant strain or a cell of the recombinant strain. The target protein may be present within the cell of the recombinant strain or secreted outside the cell of the recombinant strain, after expression depending on its type. For example, when the target protein is allulose epimerase, the allulose epimerase produced by the recombinant strain is present within the cell of the recombinant strain. A method for preparing allulose epimerase according to a preferred embodiment of the present disclosure includes expressing allulose epimerase by culturing a recombinant strain transformed by introducing an expression cassette including a polynucleotide encoding the allulose epimerase and a promoter variant operably linked thereto and consisting of a base sequence represented by SEQ ID NO: 9 or an expression vector including the expression cassette; and isolating the allulose epimerase from a lysate of the recombinant strain in which the allulose epimerase is expressed. The novel promoter variant according to one embodiment of the present disclosure is a constitutive expression vector, and thus may induce expression without using a protein expression inducer such as isopropyl-1-thio-β-D-galactopyranoside (IPTG), etc. In the present disclosure, the allulose epimerase may be recovered from the lysate of the recombinant strain. Cells used for protein expression may be destructed by various physical or chemical means such as repeated freeze-thawing, sonication, mechanical destruction or cell disintegrants, and can be isolated or purified by conventional biochemical isolation techniques (Sambrook et al., Molecular Cloning: A laboratory Manual, 2nd Ed., Cold Spring Harbor Laboratory Press, 1989; Deuscher, M., Guide to Protein Purification Methods Enzymology, Vol. 182. Academic Press. Inc., San Diego, CA, 1990). For example, methods for isolating or purifying proteins expressed by a host cell include electrophoresis, centrifugation, gel filtration, precipitation, dialysis, chromatography (ion exchange chromatography, affinity chromatography, immunosorbent affinity chromatography, reversed phase HPLC, gel permeation HPLC), isoelectric focus, and various variations or combination methods thereof, but are not limited thereto. Meanwhile, in the present disclosure, the isolating of the allulose epimerase from the lysate of the recombinant strain may be preferably performed by affinity chromatography using a peptide tag. The peptide tag may use various known tags, such as HA tag, FLAG tag, His tag, biotin carboxyl carrier protein (BCCP), c-myc tag, V5 tag, glutathione-S-transferase (GST), or maltose binding protein (MBP), preferably a double His tag. His-tagged proteins are specifically trapped on a column of nickel-nitrilotriacetic acid (Ni-NTA) resin and may be eluted with EDTA or imidazole.

The recombinant strain according to one embodiment of the present disclosure may be used to indirectly exert the function of the target protein in addition to being used to prepare the target protein. For example, when the target protein is an enzyme, the recombinant strain according to one embodiment of the present disclosure may be used to prepare a product from a substrate by an enzymatic conversion reaction. Specifically, when the target protein is allulose epimerase, the present disclosure provides a method for preparing allulose from fructose, including adding and reacting a recombinant strain to a fructose-containing solution. The recombinant strain is a host cell transformed by introducing an expression cassette including a polynucleotide encoding the allulose epimerase and a promoter variant operably linked thereto and consisting of a base sequence represented by SEQ ID NO: 9 or a base sequence represented by SEQ ID NO: 10, or an expression vector including the expression cassette, and preferably *Escherichia coli*. In addition, the fructose-containing solution may further include metal ions such as $Ca^{2+}$ and $Mn^{2+}$ to promote the activity of allulose epimerase. In addition, in the method for preparing allulose from fructose, the reaction temperature is in the range of 50 to 70° C., preferably 55 to 65° C., and more preferably 55 to 60° C. when considering smooth enzyme expression of the recombinant strain, and the stability and maximum activity of the enzyme, and the reaction pH is in the range of 6.5 to 8, preferably 6.5 to 7.5, and more preferably 6.5 to 7. In addition, in the method for preparing allulose from fructose, the concentration of fructose is not particularly limited, but preferably 1 to 75% (w/w), and more preferably 35 to 45% (w/w) based on the total reactant in consideration of productivity and economy.

Hereinafter, the present disclosure will be described in more detail with reference to Examples. However, the following Examples are only for clearly illustrating the technical features of the present disclosure, but do not limit the protection scope of the present disclosure.

Example 1: Obtainment of Promoter for Enzyme Gene Expression

Obtainment of Twin Arginine Translocase A (tatA) Gene Promoter

A twin arginine translocase A (tatA) gene promoter is a promoter for expressing a twin arginine translocase A (tatA) gene of *Escherichia coli*, and known as a promoter which consists of a base sequence represented by SEQ ID NO: 1 and induces constitutive expression in *Escherichia coli*.

In order to obtain a polynucleotide fragment corresponding to a promoter site of the tatA gene from *Escherichia coli*, PCR was performed using a genomic DNA of *Escherichia coli* MG1655 as a template and a primer set described in Table 1 below. The obtained amplified product was cloned into a pGEM-Teasy vector (Promega Co., USA) and the base sequence was analyzed, and as a result, it was confirmed that the base sequence was a polynucleotide fragment consisting of the base sequence represented by SEQ ID NO: 1 with a length of 160 bp.

TABLE 1

| Primer name | Description of primer | Base sequence of primer (5'→3') |
|---|---|---|
| PtatA-F | tatA promoter Forward promoter | ACCTGAATGGGGGTTGATGC (SEQ ID NO: 11) |
| PtatA-R | tatA promoter Reverse promoter | ACATGTTCCTCTGTGGTAG (SEQ ID NO: 12) |

1.2. Obtainment of BLMA Gene Promoter

A BLMA gene promoter is a promoter for expressing a maltogenic amylase gene of *Bacillus licheniformis*, and known as a promoter that consists of a base sequence represented by SEQ ID NO: 2 and induces stable high expression of a foreign gene in *Escherichia coli* [see TAE-JIP KIM et al (1999) Modes of Action of Acarbose Hydrolysis and Transglycosylation Catalyzed by a Thermostable Maltogenic Amylase, the Gene for Which Was Cloned from a Thermus Strain].

In order to obtain a polynucleotide fragment corresponding to a promoter site of the maltogenic amylase gene from *Bacillus licheniformis*, PCR was performed using a genomic DNA of *Bacillus licheniformis* ATCC 14580 as a template and a primer set described in Table 2 below. The obtained amplified product was cloned into a pGEM-Teasy vector (Promega Co., USA) and the base sequence was analyzed, and as a result, it was confirmed that the base sequence was a polynucleotide fragment consisting of the base sequence represented by SEQ ID NO: 2 with a length of 115 bp.

TABLE 2

| Primer name | Description of primer | Base sequence of primer (5'→3') |
|---|---|---|
| Pblma-F | BLMA promoter Forward promoter | GGTGTCTCATTCTGTTACCG (SEQ ID NO: 13) |
| Pblma-R | BLMA promoter Reverse promoter | GTTTCCCCCTTTTGGTTGTC (SEQ ID NO: 14) |

Example 2: Obtainment of Allulose Epimerase Variant Cloning Vector

The present applicants disclosed wild-type D-allulose epimerase derived from *Flavonifractor plautii* and a polynucleotide encoding the same in Korean Patent Registration No. 10-14739180. The wild-type D-allulose epimerase consisted of an amino acid sequence represented by SEQ ID NO: 3, and the polynucleotide encoding the same consisted of a base sequence represented by SEQ ID NO: 4.

In addition, the present applicants disclosed a D-allulose epimerase variant W29K/G216S/M234I with an improved conversion rate of fructose to allulose and thermal stability and a polynucleotide encoding the same in Korean Patent Publication No. 10-2021-0132405. The D-allulose epimerase variant W29K/G216S/M234I consisted of an amino acid sequence represented by SEQ ID NO: 5, in which tryptophan (Trp) present at position 29 was substituted with lysine (Lys), glycine (Gly) present at position 216 was substituted with serine (Ser), and simultaneously methionine (Met) present at position 234 was substituted with isoleucine (Ile) in the amino acid sequence of the wild-type D-allulose epimerase derived from *Flavonifractor plautii*, and the polynucleotide encoding the same consisted of a base sequence represented by SEQ ID NO: 6.

In addition, the present applicants derived a D-allulose epimerase variant W29K/A77S/G216S/M234I having excellent thermal stability under high temperature conditions and filed the application on Dec. 14, 2021 (Korean Patent Application No. 10-2021-0178690, unpublished). The D-allulose epimerase variant W29K/A77S/G216S/M234I consisted of an amino acid sequence represented by SEQ ID NO: 7, in which tryptophan (Trp) present at position 29 was substituted with lysine (Lys), alanine (Als) at position 77 was substituted with serine (Ser), glycine (Gly)

present at position 216 was substituted with serine (Ser), and simultaneously methionine (Met) present at position 234 was substituted with isoleucine (Ile) in the amino acid sequence of the wild-type D-allulose epimerase derived from *Flavonifractor plautii*, and the polynucleotide encoding the same consisted of a base sequence represented by SEQ ID NO: 8.

The polynucleotide fragment encoding the amino acid sequence of the D-allulose epimerase variant W29K/A77S/G216S/M234I was prepared using an overlap extension polymerase chain reaction method based on a polynucleotide (SEQ ID NO: 6) of a D-allulose epimerase variant W29K/G216S/M234I. Specifically, in a reaction solution added with 100 μM of deoxynucleotide triphosphates dATP, dCTP, dGTP, and dTTP, 1 μM of oligonucleotide primers (A77S forward primer and A77S reverse primer) in Table 3 below, and 100 ng of a polynucleotide (SEQ ID NO: 6) of the D-allulose epimerase variant W29K/G216S/M234I used as a template were mixed, and a PCR reaction was performed at 25 to 30 cycles in the presence of 1 unit of a pfu-X DNA polymerase mixture (Bioneer) using a Thermocycler (TP600, TAKARA BIO Inc., JAPAN). The variant fragment was amplified using a combination of primers, and then a polynucleotide fragment (SEQ ID NO: 8) encoding the amino acid sequence of the D-allulose epimerase variant W29K/A77S/G216S/M234I was finally prepared through overlap extension PCR using the amplified fragment as a template and oligonucleotide primers (NdeI forward primer and XhoI reverse primer) introduced with sequences of NdeI and XhoI restriction enzyme recognition sites in Table 3 below. Thereafter, the prepared polynucleotide fragment was inserted into the same restriction enzyme site of a pET28a vector (Novagen), using the restriction enzymes NdeI and XhoI to obtain a cloning vector.

TABLE 3

| Description of primer | Base sequence of primer (5'→3') |
|---|---|
| A77S forward primer | AATACGACCTGAGCAGCGACGATCCGGCGGTG (SEQ ID NO: 15) |
| A77S reverse primer | GATCGTCGCTGCTCAGGTCGTATTTGGCCTCCA (SEQ ID NO: 16) |
| NdeI forward primer | GCATGCCATATGAACCCGATTGGAATGCA (SEQ ID NO: 17) |
| XhoI reverse primer | GCATGCCTCGAGCGCGGTCAGCTCCTTGAGGA (SEQ ID NO: 18) |

Example 3: Preparation of Linkage Fragment of Promoter and Allulose Epimerase Variant Gene 3.1. Preparation of DNA Fragment Having Allulose Epimerase Variant Gene Linked to tatA Promoter To amplify a tatA promoter, PCR was performed using a pGEM-Teasy vector, in which the tatA promoter obtained in Example 1 was cloned, as a template and primer sets XhoI-PtatA and PtatA-FpDPE_R in Table 4 below.

In addition, in order to amplify the gene of the D-allulose epimerase variant W29K/A77S/G216S/M234I derived from *Flavonifractor plautii*, PCR was performed using a pET28a vector (Novagen), in which the gene of the D-allulose epimerase variant W29K/A77S/G216S/M234I obtained in Example 2 was cloned, as a template and primer sets PtatA-FpDPE_F and PstI-FpDPE in Table 4 below.

TABLE 4

| Primer name | Description of primer | Base sequence of primer (5'→3') |
|---|---|---|
| XhoI-PtatA | Forward primer | TTTGCGCTCGAGACCTGAATGGGGGTTGATGC (SEQ ID NO: 19) |
| PtatA-FpDPE_R | Reverse primer | TGCATTCCAATCGGGTTCATACATGTTCCTCTGTGGTAG (SEQ ID NO: 20) |
| PtatA-FpDPE_F | Forward primer | CTACCACAGAGGAACATGTATGAACCCGATTGGAATGCA (SEQ ID NO: 21) |
| PstI-FpDPE | Reverse primer | GCATGCTGCAGTTACGCGGTCAGCTCCTTGA (SEQ ID NO: 22) |

The tatA promoter fragment and the D-allulose epimerase variant gene fragment amplified in this way may be linked into one fragment due to a complementary sequence of the primer used for amplification. Overlap extension PCR was performed using the two fragments as templates and primers XhoI-PtatA and PstI-FpDPE introduced with the sequences of XhoI and PstI restriction enzyme recognition sites in Table 4 above to obtain one amplified fragment. The DNA fragment, in which the obtained tatA promoter and the gene of the allulose epimerase variant W29K/A77S/G216S/M234I were linked, was named 'PtatA-FpDPE'.

3.2. Preparation of DNA Fragment Having Allulose Epimerase Gene Linked to BLMA Promoter To amplify a BLMA promoter, PCR was performed using a pGEM-Teasy vector, in which the BLMA promoter obtained in Example 1 was cloned, as a template and primer sets XhoI-Pblma and Pblma-FpDPE_R in Table 5 below.

In addition, in order to amplify the gene of the D-allulose epimerase variant W29K/A77S/G216S/M234I derived from *Flavonifractor plautii*, PCR was performed using a pET28a vector (Novagen), in which the gene of the D-allulose epimerase variant W29K/A77S/G216S/M234I obtained in Example 2 was cloned, as a template and primer sets Pblma-FpDPE_F and PstI-FpDPE in Table 5 below.

TABLE 5

| Primer name | Description of primer | Base sequence of primer (5'→3') |
|---|---|---|
| XhoI-Pblma | Forward primer | TTTGCGCTCGAGGGTGTCTCATTCTGTTACCG (SEQ ID NO: 23) |
| Pblma-FpDPE_R | Reverse primer | TGCATTCCAATCGGGTTCATGTTTCCCCCTTTTGGTTGTC (SEQ ID NO: 24) |
| Pblma-FpDPE_F | Forward primer | GACAACCAAAAGGGGGAAACATGAACCCGATTGGAATGCA (SEQ ID NO: 25) |
| PstI-FpDPE | Reverse primer | GCATGCTGCAGTTACGCGGTCAGCTCCTTGA (SEQ ID NO: 26) |

The BLMA promoter fragment and the D-allulose epimerase variant gene fragment amplified in this way may be linked into one fragment due to a complementary sequence of the primer used for amplification. Overlap extension PCR was performed using the two fragments as templates and primers XhoI-Pblma and PstI-FpDPE introduced with the sequences of XhoI and PstI restriction enzyme recognition sites in Table 5 above to obtain one amplified fragment. The DNA fragment, in which the obtained BLMA promoter and the gene of the allulose epimerase variant W29K/A77S/G216S/M234I were linked, was named 'Pblma-FpDPE'.

Example 4: Preparation of D-Allulose Epimerase Variant Expression Vector

4.1. Preparation of D-Allulose Epimerase Variant Expression Vector Having tatA Promoter Through genetic manipulation from pTrc99A vector (Pharmacia, US), a recombinant plasmid vector including a pUC-derived replication origin capable of replicating in *Escherichia coli*, a multi cloning site (MCS) such as restriction enzyme XhoI and PstI sites, a transcription terminator, and a Kanamycin antibiotic resistance gene was manufactured. Thereafter, a D-allulose epimerase variant expression vector pPtatA:FpDPE (W29K/A77S/G216S/M234I) was prepared by cleaving the polynucleotide fragment PtatA-FpDPE prepared in Example 3 with restriction enzymes XhoI and PstI, and then ligating the polynucleotide fragment with the recombinant plasmid vector having the same restriction enzyme site. Thereafter, the D-allulose epimerase variant expression vector was transformed into *Escherichia coli* DH5a using a heat shock method (see Sambrook and Russell: Molecular Cloning) to obtain colonies with Kanamycin resistance, and five colonies were selected, and five types of recombinant expression vectors pPtatA:FpDPE (W29K/A77S/G216S/M234I) were recovered, and then the base sequence was analyzed. As a result of sequence analysis of five types of recombinant expression vectors pPtatA:FpDPE(W29K/A77S/G216S/M234I), random mutations were confirmed in the introduced tatA promoter or allulose epimerase variant W29K/A77S/G216S/M234I gene sequence, respectively, and the random mutation contents were shown in Table 6 below.

TABLE 6

| Classification of colony | Content of tatA promoter sequence mutation | Content of W29K/A77S/G216S/M234I gene sequence mutation |
| --- | --- | --- |
| Colony 1 | Corresponding to insertion of nucleotide (C) 1 bp after nucleotide (T) at position 160/ribosome-binding site (RBS) spacer mutation | Matching |
| Colony 2 | Matching | Corresponding to 1 bp deletion of nucleotide (T) at position 2/loss of start codon (ATG) |
| Colony 3 | Matching | Corresponding to 1 bp deletion of nucleotide (A) at position 10/frameshift mutation |
| Colony 4 | Corresponding to substitution of nucleotide at position 146 (C→G), substitution of nucleotide at position 148 (C→A), substitution of nucleotide at position 149 (A→G), 2 bp deletion of nucleotides (CT) at positions 159 and 160/RBS surrounding sequence mutation | Matching |
| Colony 5 | Matching | Corresponding to 1 bp deletion of nucleotide (G) at position 33/frameshift mutation and acquisition of termination codon (TGA), and transcription termination after phenylalanine at position 10 |

As shown in Table 6 above, it is expected that the recombinant expression vectors recovered from colonies 2, 3, and 5 will not be translated to prepare a desired allulose epimerase variant due to mutations in the allulose epimerase variant gene sequence. On the other hand, in the case of the recombinant expression vector recovered from colony 1, a mutation occurred in the spacer sequence located between the ribosome-binding site (RBS) of the tatA promoter and the translation start codon, and in the case of the recombinant expression vector recovered from colony 4, a mutation occurred in the sequence surrounding the ribosome-binding site (RBS) of the tatA promoter, and since the enzyme gene sequences are matched, it was determined that there was a possibility of expression of the desired enzyme. The variant promoter in the recombinant expression vector recovered from colony 1 was named 'tatAm1', and the variant promoter in the recombinant expression vector recovered from colony 4 was named 'tatAm2'. The tatAm1 promoter consisted of the base sequence represented by SEQ ID NO: 9, and the tatAm2 promoter consisted of the base sequence represented by SEQ ID NO: 10. In addition, the recombinant expression vector recovered from colony 1 was renamed 'pPtatapAm1:FpDPE (W29K/A77S/G216S/M234I)', and the recombinant expression vector recovered from colony 4 was renamed 'pPtatAm2:FpDPE(W29K/A77S/G216S/M234I)'. FIG. 1 is a cleavage map of a recombinant expression vector pPtatAm1:FpDPE (W29K/A77S/G216S/M234I) prepared in Example of the present disclosure. FIG. 2 is a cleavage map of a recombinant expression vector pPtatAm2:FpDPE (W29K/A77S/G216S/M234I) prepared in Example of the present disclosure.

4.2. Preparation of D-Allulose Epimerase Variant Expression Vector Having BLMA Promoter Through genetic manipulation from a pTrc99A vector (Pharmacia, US), a recombinant plasmid vector including a pUC-derived replication origin capable of replicating in *Escherichia coli*, a multi cloning site (MCS) such as restriction enzyme XhoI and PstI sites, a transcription terminator, and a Kanamycin antibiotic resistance gene was manufactured. Thereafter, a D-allulose epimerase variant expression vector pPblma:FpDPE (W29K/A77S/G216S/M234I) was prepared by cleaving the polynucleotide fragment Pblma-FpDPE prepared in Example 3 with restriction enzymes XhoI and PstI, and then ligating the polynucleotide fragment with the recombinant plasmid vector having the same restriction enzyme site. Thereafter, the D-allulose epimerase variant expression vector was transformed into *Escherichia coli* DH5a using a heat shock method (see Sambrook and Russell: Molecular Cloning) to obtain colonies with Kanamycin resistance, and six colonies were selected, and six types of recombinant expression vectors pPblma:FpDPE (W29K/A77S/G216S/M234I) were recovered, and then the base sequence was analyzed. As sequence analysis results of six recombinant expression vectors pPblma:FpDPE (W29K/A77S/G216S/M234I), it was confirmed that all of the vectors contained the intended BLMA promoter and the allulose epimerase variant gene sequence. FIG. 3 is a cleavage map of a recombinant expression vector pPblma:FpDPE (W29K/A77S/G216S/M234I) prepared in Example of the present disclosure.

Example 5: Preparation of Transformant with D-Allulose Epimerase Variant Expression Vector The recombinant expression vectors pPtatAm1:FpDPE (W29K/A77S/G216S/M234I), pPtatAm2:FpDPE (W29K/A77S/G216S/M234I), and pPblma:FpDPE (W29K/A77S/G216S/M234I) prepared in Example 4 were introduced into *E. coli* W3110 by the heat shock method, respectively. Thereafter, the presence of Kanamycin antibiotic resistance was confirmed, and the recombinant strains transformed with the recombinant expression vector were selected. The prepared recombinant *E. coli* was added with a glycerin solution to be a final concentration of 20% (v/v) and frozen-stored at −70° C. before performing culture for enzyme expression.

Example 6: Measurement of Conversion Rate of Fructose to Allulose by Recombinant Strains and Comparison of Enzyme Expression Intensities of Promoters Since D-allulose epimerase may convert fructose into allulose, the enzyme expression induction intensities of the respective promoters in the recombinant strain were compared by measuring the conversion rate of fructose into allulose, which was proportional to the enzyme expression amount of the recombinant strain.

In order to culture the recombinant *E. coli* transformed with the recombinant expression vector, 100 ml of an LB medium containing Kanamycin at a final concentration of 50 µg/ml was contained in a 1 L flask, and 1 ml of the recombinant *E. coli* prepared in Example 5 was inoculated therein. Thereafter, the flask was transferred to a shaking incubator, and the recombinant *E. coli* was cultured for 14 hr while maintaining a temperature condition of 30° C. and a shaking condition of 140 rpm, and the culture medium was centrifuged to collect the cells. Thereafter, the recovered cells were added at a concentration of 1 mg/mL to a 50 mM PIPES buffer solution (pH 7.0) containing 30% (w/w) fructose and 1 mM manganese sulfate ($MnSO_4$) metal ions, and the reaction was performed at 62° C. for a predetermined time, and then the temperature of the reaction product solution was lowered to 4° C. to stop the reaction, and centrifugation was performed under conditions of 16,600×g and 4° C. to recover the supernatant. Thereafter, the concentrations of allulose and fructose in the supernatant were measured using high-performance liquid chromatography (HPLC), and the conversion rate of fructose to allulose was calculated from the measured results, and the conversion rate was used as an indicator of enzyme activity. FIG. 4 illustrates a conversion rate according to a reaction time when the conversion reaction of fructose to allulose is performed using recombinant *Escherichia coli* prepared in Example of the present disclosure. In FIG. 4, 'PtatAm1' represents recombinant *Escherichia coli* transformed with the recombinant expression vector pPtatAm1:FpDPE (W29K/A77S/G216S/M234I), 'PtatAm2' represents *Escherichia coli* transformed with the recombinant expression vector pPtatAm2:FpDPE (W29K/A77S/G216S/M234I), and 'Pblma' represents *Escherichia coli* transformed with the recombinant expression vector pPblma:FpDPE (W29K/A77S/G216S/M234I). As shown in FIG. 4, the recombinant *Escherichia coli* into which the tatAm1 promoter was introduced and the recombinant *Escherichia coli* into which the tatAm2 promoter was introduced showed a much higher conversion rate of fructose into allulose than the recombinant *Escherichia coli* into which the BLMA promoter was introduced. From these results, it can be seen that the enzyme expression induction effect of the tatAm1 promoter and the tatAm2 promoter are much stronger than that of the BLMA promoter. In addition, meanwhile, since the expression intensity of the target gene by the constitutive expression promoter is too strong, a load may be caused on the recombinant strain, even if the expression intensity by the tatAm1 promoter is somewhat lower than that by the tatAm2 promoter, the tatAm1 promoter is considered more advantageous in a commercial aspect.

As described above, the present disclosure has been described through Examples above, but the present disclosure is not necessarily limited thereto, and various modifications can be made without departing from the scope and spirit of the present disclosure. Therefore, the scope of the present disclosure should be construed to include all embodiments falling within the scope of claims appended hereto.

The invention claimed is:

1. A promoter variant consisting of a base sequence of SEQ ID NO: 9 or a base sequence of SEQ ID NO: 10.

2. A recombinant vector comprising the promoter variant of claim 1.

3. An expression vector comprising a polynucleotide encoding a target protein and the promoter variant of claim 1 operably linked thereto.

4. The expression vector of claim 3, wherein the target protein is an enzyme.

5. The expression vector of claim 4, wherein the enzyme is allulose epimerase.

6. The expression vector of claim 5, wherein the allulose epimerase consists of an amino acid sequence of SEQ ID NO: 3, the amino acid sequence of SEQ ID NO: 5, or the amino acid sequence of SEQ ID NO: 7.

7. The expression vector of claim 5, wherein the polynucleotide encoding the allulose epimerase consists of a base sequence of SEQ ID NO: 4, a base sequence of SEQ ID NO: 6 or a base sequence of SEQ ID NO: 8.

8. A recombinant strain transformed with the expression vector of claim 5.

9. A method for preparing allulose from fructose, comprising adding and reacting the recombinant strain of claim 8 to a fructose-containing solution.

* * * * *